(12) United States Patent
Hao (10) Patent No.: US 8,235,900 B2
(45) Date of Patent: Aug. 7, 2012

(54) METHOD AND APPARATUS FOR AN AUTOMATIC ULTRASOUND IMAGING SYSTEM

(75) Inventor: Xiaohui Hao, Blaine, WA (US)

(73) Assignee: ImSonic Medical, Inc., Blaine, WA (US)

( * ) Notice: Subject to any disclaimer, the term of this patent is extended or adjusted under 35 U.S.C. 154(b) by 302 days.

(21) Appl. No.: 12/409,408

(22) Filed: Mar. 23, 2009

(65) Prior Publication Data

US 2010/0240992 A1    Sep. 23, 2010

(51) Int. Cl.
*A61B 8/00* (2006.01)

(52) U.S. Cl. ........ 600/437; 375/296; 600/443; 600/458; 600/447; 600/455

(58) Field of Classification Search .......... 600/437–461, 600/407
See application file for complete search history.

(56) References Cited

U.S. PATENT DOCUMENTS

| | | | |
|---|---|---|---|
| 6,102,859 A | 8/2000 | Mo | |
| 6,508,774 B1 | 1/2003 | Acker | |
| 7,578,792 B2* | 8/2009 | Lee et al. | 600/453 |
| 7,848,449 B2* | 12/2010 | Nagatani et al. | 375/296 |
| 2003/0045797 A1* | 3/2003 | Christopher et al. | 600/453 |
| 2006/0173311 A1 | 8/2006 | Hao | |
| 2006/0173312 A1* | 8/2006 | Jackson et al. | 600/437 |
| 2006/0241455 A1* | 10/2006 | Shvarts | 600/447 |

* cited by examiner

*Primary Examiner* — James Kish
*Assistant Examiner* — Michael N Fisher
(74) *Attorney, Agent, or Firm* — Christensen O'Connor Johnson Kindness PLLC (57) ABSTRACT

An ultrasound imaging system that can automatically adjust the imaging parameters based on the original or processed received echoes from the target is presented in this disclosed technology. The adjustment is done through a closed loop negative feedback control system iteratively. Imaging performance evaluation parameters calculated from the received echoes, original or processed, are compared with preset thresholds that represent desired optimal imaging performances. The differences are used to calculate the adjustment for the imaging parameters. The system reaches to an optimal system image quality for the current target or stops when a maximum number of iterations is reached.

24 Claims, 9 Drawing Sheets

▲ Measured SNR at different depth

■ SNR threshold at different depth

↕ ΔSNR at different depth between two least square fitted curves

METHOD AND APPARATUS FOR AN AUTOMATIC ULTRASOUND IMAGING SYSTEM

BACKGROUND

Ultrasound imaging is becoming more and more widely used in clinical care due to its non-invasive, no radiation, portable and low-cost characteristics compared to other imaging modalities such as CT, MR, and PET. Together with its fast growing usage, more and more clinical staffs are getting access to ultrasound imaging systems. This brings a big challenge to the health care system since ultrasound imaging system is one of the most complicated medical imaging systems to use due to the tissue dependence of the ultrasound wave propagations.

As a mechanical wave, ultrasound wave propagation is affected by a number of facts such as the tissue scattering and absorption, variations in propagation speed and dispersion in tissue. As a result, ultrasound imaging in human tissue suffers from loss and defocusing of the propagating energy which varies substantially from patient to patient. Thus, many controls are needed to allow customers to adjust the transmit and receive paths when imaging different patients. Typical ultrasound imaging systems usually have a big control console with many control buttons. Given the need to adjust a number of imaging controls through the console, each patient's ultrasound scan can take 20 to 40 minutes even for experienced clinicians. The required exam time can be even longer for a clinician who is not familiar with the ultrasound controls. This severely affects the clinical efficiency and slows down the clinical work flow, thus affecting the profitability of the health care system. Further, it takes about 1-2 years for a fresh clinical student to be trained to operate an ultrasound imaging system to get the proper images needed for diagnosis. This is a burden that most of the new ultrasound customers cannot afford. On the contrary, the other imaging modalities, such as CT and MR, are much easier to use. Their image quality is not affected by tissue properties, thus, eliminating the need for complicated imaging control adjustments. Given these problems, there is a need to have an ultrasound imaging system that is as simple to operate as a CT or MR system, with little or no user involvement in the imaging process.

Numerous solutions to the above-described problem have been proposed. For example, many high-end ultrasound systems have imaging presets created in-house based on different patient types. A user can select one of the settings when a patient with an obesity problem is being scanned, or select another setting when a thin patient is being scanned. These pre-set imaging parameters certainly help the image quality and reduce the number of adjustments needed. However, these settings are hard to create in-house due to the lack of the pathologies. In addition, if the patient's pathology differs from the pre-set pathology, which happens frequently, these settings do not perform well. Some prior art devices have tried to use patient information to adjust the settings. For example, a gain adjustment in B mode imaging has been presented by Larry Mo., in U.S. Pat. No. 6,102,859, Method and Apparatus for Automatic Time and/or Lateral Gain Compensation in B-mode Ultrasound Imaging. This patent describes the use of current tissue echo intensity to adjust the system gain distribution. In U.S. Pat. No. 6,508,774, to Acker et al., a HIFU system with feedback control is disclosed, where a feedback signal identifies cavitations and the system then moves the HIFU focus away from the cavitations to avoid further damage. In another example, Hao, et al., in U.S. Patent Application No. 20060173311, Method and System for Controlling an Ultrasound System, introduces feedback control of acoustic power output to reach a certain MI value in micro-bubble contrast imaging. However, how this idea can be extended to general ultrasound imaging remains unknown. So far, there is no smart system that can adjust the imaging parameters automatically to reach the best performance of the system for each particular patient in all aspects.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

To address the above-cited problems and others, this disclosed technology presents an automated ultrasound imaging system having a built-in negative feedback control loop (closed-loop control subsystem) in the system architecture. When the system is scanning a new target or an imaging condition has been changed when the system is scanning the same target, this negative feedback control loop automatically adjusts one or more of the imaging parameters based on the received echoes from the target and the pre-stored expected performance evaluators.

In one embodiment, the negative feedback control loop is constructed with the following components: an ultrasound imaging unit, which sends ultrasound waves into the target and receives and processes the reflected echoes, and an ultrasound system control unit that controls the ultrasound imaging unit. The received data is sent to a performance evaluation parameter calculator to calculate evaluation parameter values. The calculated evaluation parameter values are then compared with predetermined thresholds by a comparator and the differences are sent to a feedback control logic unit. A difference and feedback control decision then starts the adjustment of the current imaging parameters. The adjustment is calculated from the differences with the aim to reduce the differences to zero. The adjusted imaging parameters are sent to the ultrasound system control to start a new imaging control iteration. This process repeats until a good imaging performance or a maximum number of iteration times is reached.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Closed-loop control systems (Feedback control systems) are found in abundance in all sectors of industry, such as quality control of manufactured products, automatic assembly lines, machine-tool control, space technology, transportation systems, power systems, robotics, and many others. In a typical closed-loop control system, a sensor monitors the system output and feeds the measured data to a controller, which continuously adjusts the system input as necessary to keep the control error to a minimum (to maintain the reference system output). Feedback on how the system is actually performing allows the controller to quickly reach the targeted stable response during setup, and also allows the controller to dynamically compensate for disturbances to the system. An ideal feedback control system cancels out all errors between desired output and real output in a short transition time, effectively mitigating the effects of any forces that may or may not arise during operation and producing a response in the system that perfectly matches the user's wishes.

In ultrasound imaging, there exists a relatively common understanding of desired imaging performance, such as a good signal-to-noise ratio (SNR) in deep depth, a good image detail resolution, a good image contrast resolution, a good image detail and contrast resolution uniformity through image depth and width, a good color flow sensitivity, a good Doppler sensitivity, a good imaging frame rate, and many others. As described in the introduction section, changes of the target tissue property force the user to make many control adjustments per each particular target on the fly to reach the desired imaging performance. This consumes a lot of time. To reduce the time required to complete an exam or ease the use of the imaging system, this disclosed technology includes a closed-loop feedback control scheme that is incorporated into ultrasound imaging to reach a desired imaging performance automatically regardless of the target tissue properties.

Figure 1:
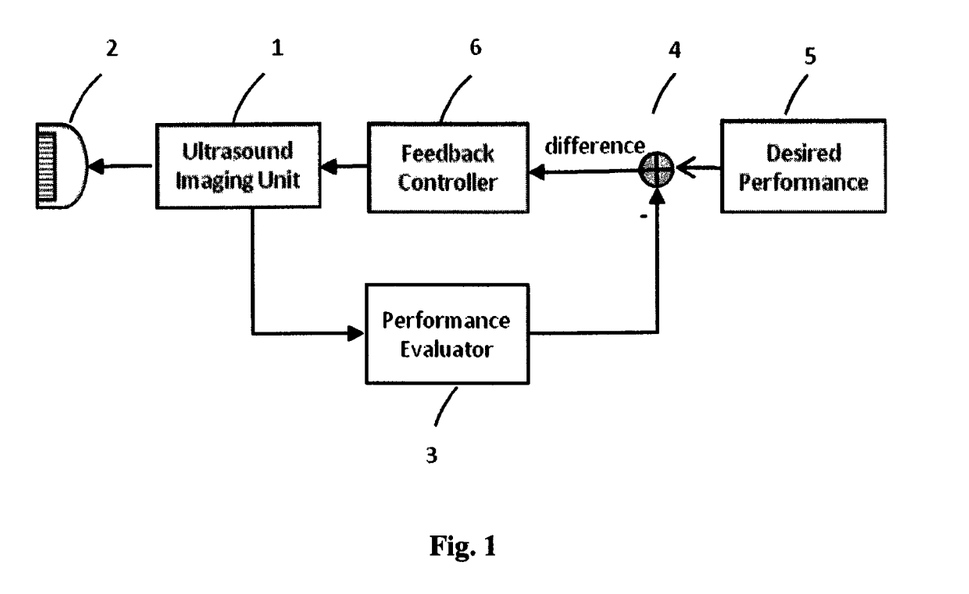
FIG. 1 is a conceptual block diagram of the closed-loop control ultrasound imaging system of the disclosed technology.

FIG. 1 shows the conceptual block diagram of a closed-loop control ultrasound imaging system. The system is constructed by a regular ultrasound imaging unit 1, which sends and receives signal to/from the target through transducer 2. Before or after processing, the received signal is sent to a performance evaluator 3, which evaluates the ultrasound imaging performance and sends evaluation results to comparator 4 to compare with a pre-stored desired performance. A systems feedback controller 6 receives one or more differences from the comparator 4 and adjusts one or more imaging parameters accordingly in the aim to reach the desired imaging performance. The new imaging parameter settings are sent to the ultrasound imaging unit 1 to start imaging again. This process iterates until the desired performance is reached or a maximal number of allowed iteration times are reached.

Given the real time imaging requirement in ultrasound imaging, one embodiment of the closed-loop feedback control system does not check the imaging performance continuously as in regular industrial applications. Rather, the closed-loop control system is mainly targeted on driving the system into a desired performance state with a fast transient response when a major imaging condition change happens. When the user makes one or more changes related to the imaging control, such as a depth change, a frequency change, a focal zone number change, a focal zone position change, an imaging mode change, an image field of view change, a Doppler gate size change, etc., or the user starts an imaging mode (i.e., B mode, Color Flow mode, Pulse Wave Doppler mode, Continuous Wave Doppler mode, 4D imaging mode, Elastography imaging mode, Contrast imaging mode, a Duplex or triplex mode, etc.) on a target, the automatic control process is triggered and this ultrasound system automatically sets the imaging parameters through several feedback control iterations to reach a desired optimal imaging performance for the current target. This may include an iterative process to select a good tradeoff between signal-to-noise ratio (SNR) and detail/contrast resolution, or an iterative process to select a proper color Pulse Repetition Frequency (PRF), or an iterative process to select a well balanced imaging gain, a good display map and an iterative process to select the proper transmit and receive frequency, an iterative process to select a good combination of focal zone numbers and frame rate, an iterative process to select a tradeoff between pulse repetition frequency and acoustic decay, etc. In each iterative process, the system analyzes the original or processed received echoes to decide whether the desired imaging performance has been reached and then adjusts imaging parameters accordingly. This automatic adjustment process can also be triggered by a timing control so the feedback process is turned on automatically at certain time intervals.

Figure 2:
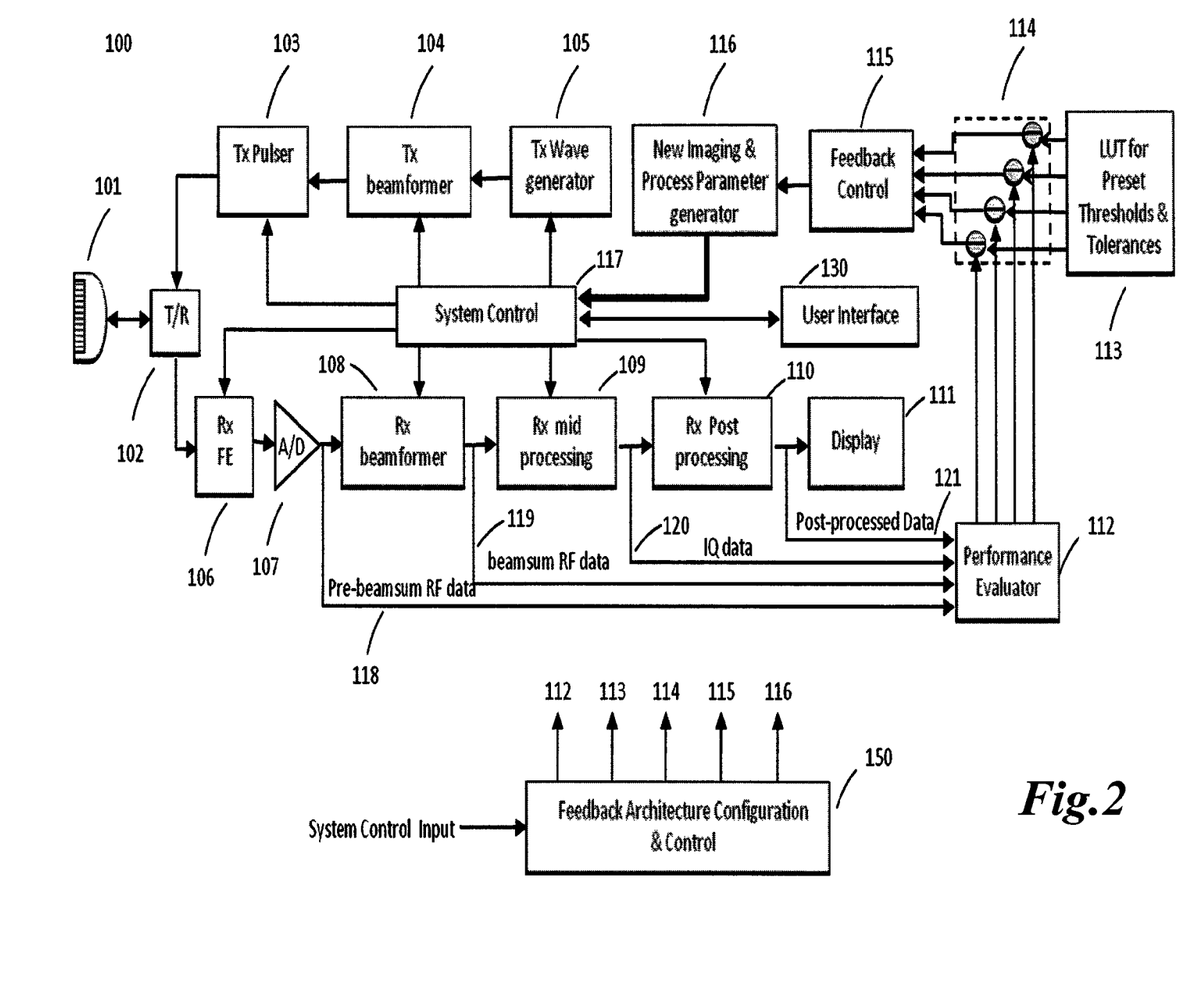
FIG. 2 is a block diagram of the automated ultrasound imaging system in accordance with one embodiment of the disclosed technology.

In accordance with one embodiment of the disclosed technology, FIG. 2 shows a detailed block diagram of an automated ultrasound imaging system 100. In this system, a transmit waveform is generated by the Tx wave generator 105, and beamformed by a Tx beamformer 104. A Tx pulser 103 creates the final pulse and sends it to a transducer 101 through a T/R switch 102. An ultrasound signal is transmitted through an ultrasound transducer 101 into the target. The reflected echoes are received by the same transducer 101 with multiple available channels on the system. Each of the received multi-channel signals passes the T/R switch 102 and is sent to receive front end circuitry 106 for amplification before being converted to digital signal by an A/D converter 107. The multi-channel digital radio frequency (RF) signals are beamformed to form a beamsummed RF signal in a Rx beamformer 108. The RF signal is demodulated, down sampled and low pass filtered in a mid processor 109. The output of mid processor 109 is in-phase and quadrature (IQ) data. An Rx post processor 110 applies necessary signal processing on the input IQ data to produce image data for different modes. In detail, the Rx post processor 110 applies envelope detection, log compression, and other image enhancement processing techniques to get B mode image data. It applies phase extraction processing to get velocity and variance info for blood flow imaging. It also applies Fourier transformation processes for Pulse Wave Doppler, volume rendering for 4D imaging, speckle tracking for Elasticity imaging, and dynamic range compression for M mode imaging. The output of the Rx post processor 110 is sent to a display viewer 111. System control unit 117 sends imaging and processing instructions to units 101 to 110, and it also receives from or sends instructions to a user interface (i.e., a console) 130. All the above components are common to normal ultrasound imaging systems and are therefore not discussed in further detail.

In the ultrasound system disclosed, certain imaging performance evaluation parameters (or, in short, evaluation parameters) are calculated using system available data, which can include, but are not limited to, the pre-beamsummed multi-channel RF data transferred through a data bus 118, or the beamsummed RF data transferred by a data bus 119, or the mid processed IQ data transferred by a data bus 120. In other embodiments, the data can be further processed image or flow, Doppler data transferred through a data bus 121. These data are transferred to a performance evaluator 112 where system imaging performance evaluation parameters (evaluation parameters) are calculated. The evaluation parameters represent imaging performance aspects that are important for imaging diagnosis e.g., SNR in depth, system gain distribution, image detail and contrast resolution, Color Flow Sensitivity, image detail and contrast resolution uniformity, Color Flow wall overwriting, imaging frame rate, etc.

In one embodiment, each time these performance evaluation parameters are calculated, they are compared with corresponding pre-stored performance evaluation parameter thresholds through a multi-subtractor 114. These thresholds represent desired imaging performances and are saved in, for example, the Look-Up table (LUT) 113 or other computer readable storage mechanism. The differences, $\Delta$parameters, and the number of iteration times are checked in a feedback control block 115 where the $\Delta$parameters need to satisfy the logic condition that $\Delta$parameters should fall in a range defined by the tolerance values as $\Delta$parameters$\in$(−tolerances~+tolerances) or described as the absolute values of $\Delta$parameters should be smaller than the tolerances: |$\Delta$parameters|<tolerances, to claim satisfaction of desired imaging performances. Here, tolerances are preset values to control how close the desired imaging performances should be approached. If logic conditions are not satisfied, $\Delta$parameters will be output to the new imaging & process parameter generator 116 to adjust the value of one or more imaging parameters for the purpose of driving $\Delta$parameters toward zero to fall within the tolerance ranges, thus, approaching the desired imaging performances. The performance evaluator 112, the multi-subtractor 114, the feedback control unit 115 and the new imaging & process generator 116 together form the system negative feedback controller shown as block 6 in FIG. 1.

In certain implementations of this automatic feedback loop control process, more than one imaging performance evaluation parameter can be evaluated by the performance evaluation data processor 112. Each evaluation parameter results in a $\Delta$parameter, and corresponds to a set of one or more imaging parameters whose values need to be adjusted. Different sets of imaging parameters that correspond to different $\Delta$parameters may partially overlap or interfere with each other. When one $\Delta$parameter drives an imaging parameter to one value, another $\Delta$parameter may drive the same imaging parameter to another value. In another case, an adjustment of one imaging parameter for one $\Delta$parameter may interfere with the adjustment of another imaging parameter corresponding to a different $\Delta$parameter. The new imaging & process parameter generator 116 has to decide which adjustment to apply to the system. To solve this issue, the feedback control unit 115 also checks the importance of each particular imaging performance aspect for clinical diagnosis. In case there is a conflict of two or more adjustments for the same imaging parameter value, the system selects the adjustment initiated from the evaluation parameter corresponding to the imaging performance aspect with the highest importance for diagnosis. The importance of each imaging performance aspect among all the imaging performance aspects that are involved in current feedback control is determined through investigation on opinions of a large amount of clinicians.

The importance is also checked by the feedback control 115 when more than two evaluation parameters are employed. In an embodiment where two evaluation parameters are presented, both evaluation parameters have to meet the requirement that the absolute value of the differences ($\Delta$parameters) should be smaller than the preset tolerances to halt further iterations of the feedback control. In an embodiment where there are three evaluation parameters used in the feedback system, the preset control logic needs to satisfy two conditions: first, the evaluation parameter representing the imaging performance aspect with the highest importance for diagnosis among the three must meet the requirement |$\Delta$parameter|<tolerance; second, at least two evaluation parameters satisfy the requirement |$\Delta$parameter|<tolerance.

In an embodiment where there are more than three performance evaluation parameters, the system separates all the desired imaging performance aspects into two or more imaging performance sets and each set has at most three evaluation parameters. Further, each imaging performance set has its own group of imaging parameters to modify. Groups of imaging parameters for different imaging performance sets do not conflict or overlap. The system will then reach the overall imaging performance through sequentially applied, multiple feedback control processes. Each feedback control process reaches at most three desired imaging performance aspects following the control logic described above. In one embodiment, the different imaging performance sets are independent. For example, in B and Pulse Wave Doppler Duplex mode, the desired imaging performance aspects can be separated into two sets: the B mode imaging performance set that includes the B mode SNR, B mode detail and contrast resolution, and B mode image uniformity; and the Pulse Wave Doppler imagining performance set, which includes Pulse Wave Doppler sensitivity, Pulse Wave Doppler resolution, etc. These two imaging performance sets have no dependence on each other. The system can run the control process for each set separately in random order and reach overall imaging performance eventually. In another embodiment, one imaging performance set may be dependent on another imaging performance set. For example, in case of Color Flow imaging, the desired imaging performance aspects can be separated into the basic imaging performance set, which includes the CF SNR, the CF image resolution, the CF image uniformity, and a color special imaging performance set that includes the color sensitivity. The color sensitivity performance is affected by the basic imaging performance, such as the CF SNR performance, beyond the color special imaging parameters, such as PRF and wall filter. Thus, the system adjusts the basic imaging performance set first to settle the basic SNR, then runs the control process to satisfy the color sensitivity requirement. As another example, in B mode imaging, the system may adjust the SNR, image resolution, image resolution uniformity first in one feedback control process, and then adjusts the gain uniformity in a following feedback control process since the gain distribution is dependent on the basic imaging performance.

In the above embodiment, where three evaluation parameters are chosen to be a turnover number, it is understandable that other number of evaluation parameters can be chosen per the requirement of the particular imaging case. For example, instead of three, four evaluation parameters may be chosen to be the turnover number. In this case, the control logic needs to have at least three evaluation parameters meet the requirement |$\Delta$parameter|<tolerance including the most important one to halt further iterations of the feedback control.

In one embodiment of the disclosed technology, the importance of each imaging performance aspect is defined as a priority number and is combined with each evaluation parameter. The higher the importance, the higher the priority an imaging performance aspect will be assigned. In another embodiment, the tolerance serves as an importance parameter, and is defined based on the importance of that particular imaging performance aspect in clinical diagnosis. The more important, the less the tolerance value is. In case there is a conflict of two or more adjustments for the same imaging parameter value, the adjustment that results from the evaluation parameter with a less or the least tolerance value is applied.

In one embodiment of this disclosed technology, the pre-stored evaluation parameters' thresholds and tolerances are acquired empirically in-house by scanning large number of models based on clinical applications. Some are acquired directly; most are calculated from the best setting selected by in-house clinicians. For example, when a clinician is satisfied by an imaging performance, the imaging setting and the tissue characteristics are used to calculate the expected SNR values at different depths. However, due to the lack of different pathologies, which is the common case, these in-house determined thresholds do not necessarily represent an optimal image quality. Further, users may value imaging performances differently than in-house clinicians, so they may have different opinions about the tolerance values. In another embodiment of this disclosed technology, the thresholds and tolerances are set onsite by users following a predefined procedure on a patient image database. Any thresholds and tolerances set by a user may be stored in a memory for access by the multi-subtractor 114 and feedback control 115. In yet another embodiment of this disclosed technology, some of the thresholds and tolerances may be calculated with the received echoes on the fly such as the color flow sensitivity described below in one embodiment of this disclosed technology.

The closed-loop control system has the ability to automatically correct the adjustment of imaging parameters. Assuming a change in an imaging parameter actually produces a worse image, then the absolute values of the Δparameters actually go up in the following iteration. The feedback logic then operates to adjust the imaging parameters in the opposite way to drive the Δparameters toward zero, thus correcting the wrong adjustment in the previous iteration. The adjusted imaging parameters are sent to system control 117 from the new imaging & process parameter generator 116. The system control 117 then distributes these parameters to the different imaging functional blocks. For example, a receive analog control change is sent to the receive front end circuits 106, a transmit pulse amplitude change is sent to the Tx pulser 103, a new transmit waveform is sent to the Tx wave generator 105, a transmit aperture change is sent to the Tx beamformer 104, a receive aperture and apodization change is sent to the Rx beamformer 108, a receive low pass filter bandwidth change is sent to the mid-processing block 109, and a receive post processing change is sent to the Rx post processor 110. The system then restarts imaging with these new imaging parameters. The newly received echoes, original or processed, are sent to the performance evaluator 112 per feedback control requirement and a new iteration starts. This negative feedback control iteration can repeat continuously until one of two conditions is met: the feedback control logic is satisfied (i.e., |Δparameters|<tolerances), which means a stable response has been reached and a desired image quality is expected or when the number of iteration times reaches a maximum allowed number and further iteration ends with a trivial solution.

There are many applications of this automated closed-loop control ultrasound imaging system. In different applications, the feedback control architecture keeps the same form. However, the detailed configuration of each functional block, including the performance evaluator 112, the look up table 113, the multi-subtractor 114, the feedback control 115 and the new imaging & process parameter generator 116 can be reconfigured specifically for a particular application. Further, the automatic adjustment process may also be reconfigured accordingly. In FIG. 2, the feedback architecture configurations & control 150 contains (stores) a set of configurations for applications on different imaging modes such as an automated B mode imaging configuration, an automated M mode configuration, an automated 4D imaging configuration, an automated Color flow imaging configuration, an automated Pulse/Continuous Wave Doppler imaging configuration, an automated Elastography imaging configuration; and for applications on different patient types such as a sound speed change configuration for breast scanning; and for applications on advanced imaging features such as a steering angle adjustment for steered spatial compounding imaging, a system power output adjustment for contrast imaging, etc. When the system or a user decides to reconfigure the feedback control loop, the system control sends a command to the feedback architecture configuration & control 150 to modify one or more of the components from 112 to 116 in the feedback control architecture per the coming application. Each specific configuration is targeted on a set of one or more specific imaging performance issues and can be combined and executed in serial or in parallel to meet an overall imaging performance requirement. In case multiple reconfigurations are necessary, the system determines an execution order based on predefined control saved in the feedback architecture configuration & control 150.

The feedback architecture configuration & control 150 also serves as the starter of the feedback control process. When the user changes an imaging mode or an imaging control of the imaging system, the system control 117 detects the change and passes the information to the feedback architecture configuration and control 150, which then starts the whole negative feedback control process. These imaging controls such as depth, image field of view, transmitting frequency, focal zone position, number of focal zones, Doppler gate size, Color Flow PRF, output power level, TGC pot gain, etc., have significant effects in the system imaging chain. In another embodiment, a timing control in the feedback architecture configuration & control 150 can also turn on the feedback control process at a predetermined time intervals.

In one embodiment, the performance evaluator 112, the multi-subtractor 114, the feedback control 115, the new imaging & process parameter generator 116 and the feedback architecture configuration & control 150 are implemented by one or more programmable or special purpose processors that execute programmed instructions to implement the functions described. Alternatively, the system control 117 can be programmed to implement the functions of these blocks. In yet another alternative embodiment, a remote computer system (not shown) can interface with the ultrasound system via a wired or wireless communication link to provide the feedback control system.

Figure 3:
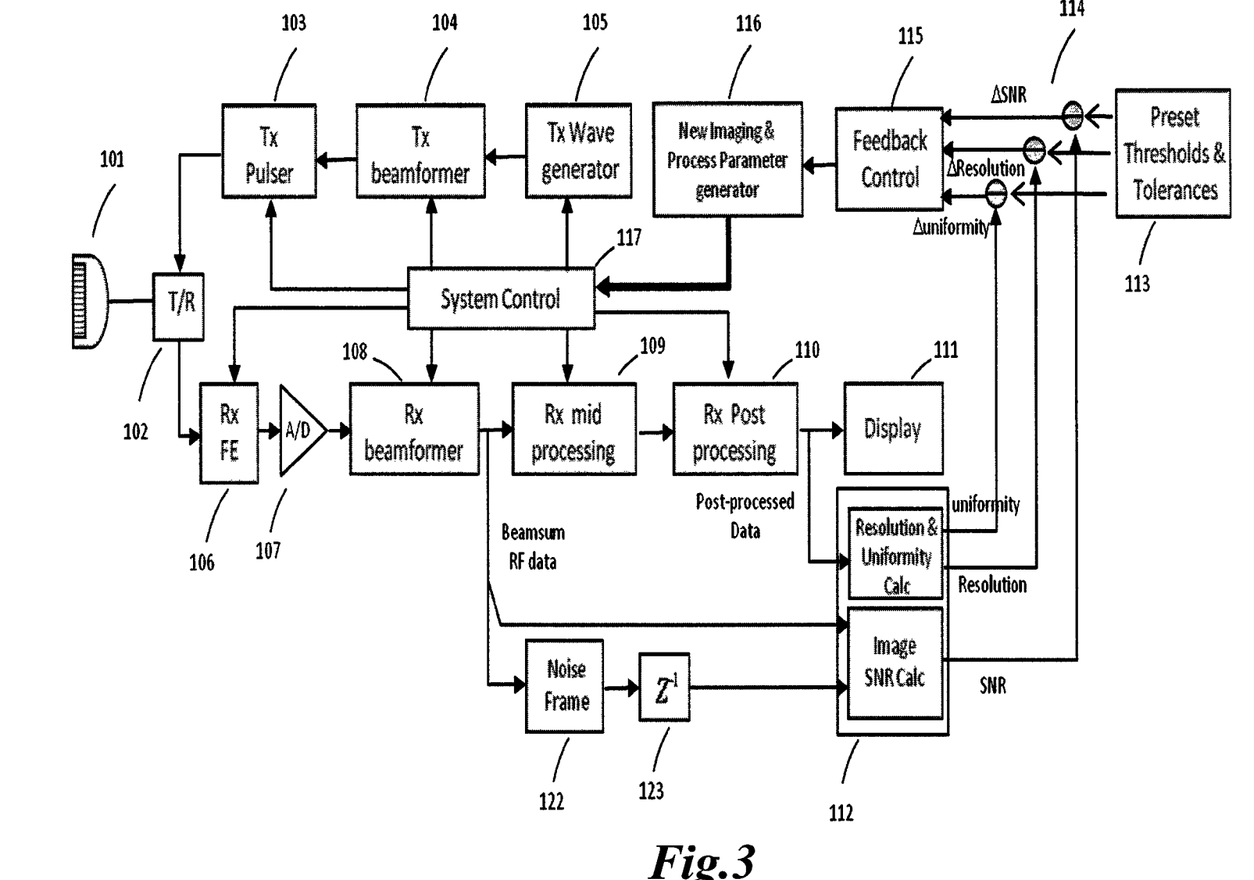
FIG. 3 is a configuration block diagram of one embodiment of a system feedback control loop for automated B mode imaging.

Several special feedback control loop configurations are set forth in detail below as examples. The first example is an automated B mode imaging configuration with the block diagram shown in FIG. 3. When a user makes a change that affects B mode imaging, such as an image geometry change or an image application change (i.e., from a vascular scan to a small parts thyroid scan, or from an abdomen scan to an OB scan, etc.), this disclosed system adjusts one or more of the imaging parameters such as the transmit frequency, receive bandwidth, transmit and receive F number, receive center frequencies in depth, number of focal zones, focal zone positions, image gains, etc., by checking one or more of the imaging performance evaluation parameters such as SNR, image resolution, image resolution uniformity, image gain distribution through the negative feedback control loop using the first several firings. A priority of performance importance is set from high to low as SNR>image uniformity>image resolution. Using tolerance values to define the performance importance, the tolerance values from high to low are: image resolution>image uniformity>SNR. This priority setting is done per preference of a majority of clinicians. The tolerance value is sent to the feedback control 115 and the new imaging & process parameter generator 116 from the look-up table 113 through the multi-subtractor 114. In FIG. 3, two new blocks, a noise frame buffer 122 and a digital delay 123, are added to the feedback control path. The noise frame buffer 122 saves the noise frame acquired at iteration time $I_{t-1}$ before acquisition of a normal frame with current imaging settings. In this example, the noise frame contains beam-summed RF data from the Rx beamformer 108. In another embodiment, the noise frame contains demodulated IQ data and the noise frame buffer 122 gets data from the Rx mid processor 109. This noise frame is delayed by one iteration in the digital delay $Z^{-1}$ block 123. Then the noise frame is compared with the normal transmission frame acquired at iteration time $I_t$ to calculate SNR at different depths in the performance evaluator 112. Other parameters, such as the image detail/contrast resolution, the resolution and gain distribution uniformity are calculated using post-processed data in the performance evaluator 112. These three outputs are then compared with pre-stored thresholds in multi-subtractor 114. Then, the differences are output to the feedback control 115, where the feedback control logic for three evaluation parameters mentioned above is applied. If further adjustment is needed, the differences are sent to the new imaging and process parameter generator 116 to adjust the imaging parameters.

Figure 4:
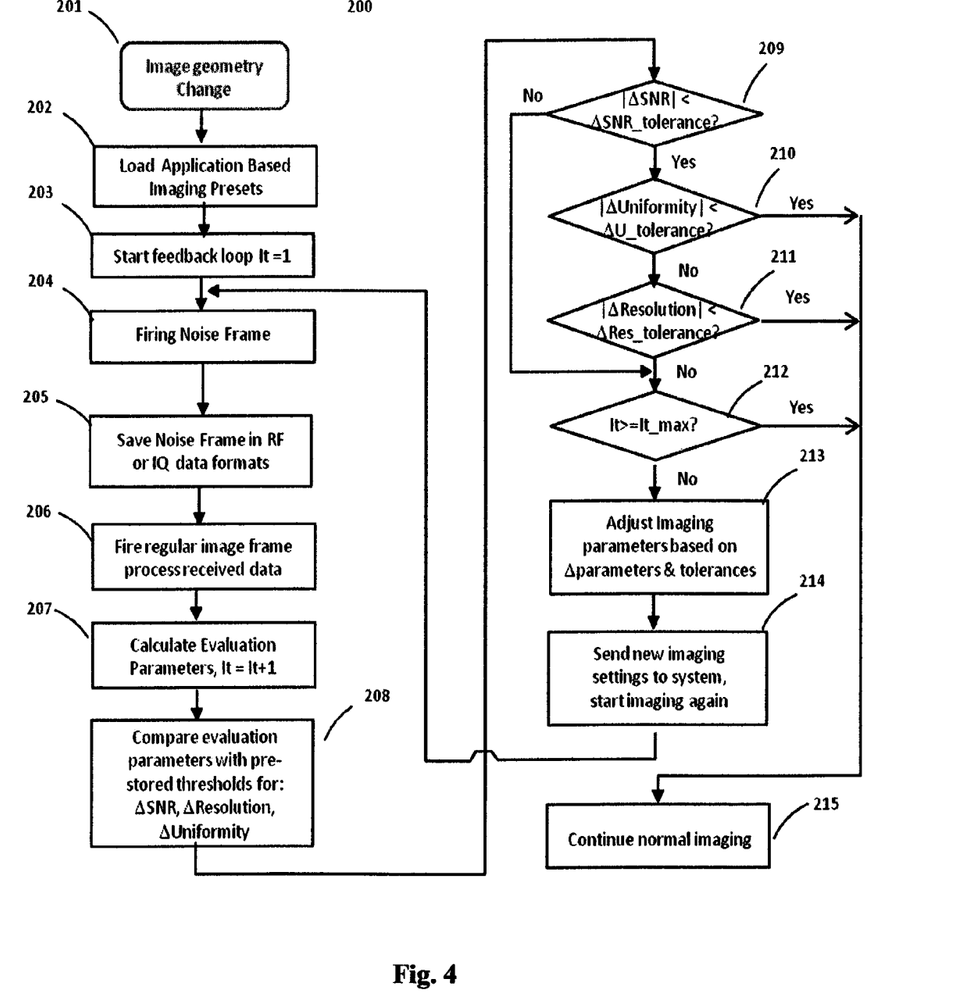
FIG. 4 is a workflow diagram of an image geometry change for automated B mode imaging in accordance with one embodiment of this disclosed technology.

FIG. 4 illustrates one example embodiment of a detailed workflow 200 for an image geometry change of this automatic B mode imaging application. After an image geometry change in 201, the system loads clinical application based, pre-stored imaging presets in 202, sets the initiative iteration index, and starts the feedback iteration in 203. Then, the system acquires the first image with transmission turned off in 204. The acquired RF and IQ data are saved in step 205 as a baseline noise frame. In step 206, the system acquires normal image data with the transmit turned on. For this acquisition, in both transmit and receive, the system uses exactly the same imaging parameters as in the acquisition of the noise frame. Evaluation parameters, in this case, the SNR at different depths, the detail & contrast resolution at different depths, the image resolution and gain uniformity, are calculated in step 207, and are compared with pre-stored thresholds to get the differences in step 208. In one embodiment, there is no particular order for calculation and comparison of evaluation parameters in step 207 and 208. In another embodiment, the calculation and comparison of the evaluation parameters are implemented in series. The iteration time index is increased in step 207. Feedback control block 115 compares the differences with preset tolerances in steps 209, 210 and 211 using a preset control logic and then determines if the system has reached an expected performance or not. The preset tolerances used in feedback control block 115 are set based on large amounts of clinical imaging practices.

The steps 209, 210 and 211 in this embodiment give an example of the three evaluation parameter control logic described before. Given the logic and the tolerance values, if the |ΔSNR|<ΔSNR_Tolerance, and any one of the image uniformity or image resolution conditions is satisfied, the system knows that the desired imaging performance is reached. Otherwise, further adjustment is needed. In detail, a failure of ΔSNR check in step 209 turns the system to step 212 directly for maximum iteration time check. If answers to steps 209 and 210 are yes, the system can jump out of the iteration loop and go to step 215 to start regular imaging with the current imaging parameters. Positive answers to 209 and 211 only lead to the same result. A failure on either of these two conditions guides the system to step 212 for maximum iteration time check. In 212, if the maximal allowed number of iteration times is reached, the system stops the iteration and jumps to step 215. If not, at the new imaging & process parameter generator 116, the system recalculates the imaging parameters such as the transmit frequency, the transmit and receive aperture control, the receive filter center frequency and bandwidth, etc., in the aim to decrease the differences. The paragraphs below details the calculation of SNR, detail resolution, detail resolution uniformity and adjustment based on them.

In one embodiment of the automatic B mode imaging control process, SNR at different depths are calculated using beamsummed RF data from the Rx beamformer 108 as: $SNR_d = Inten\_norm_d / Inten\_noise_d$, where $Inten\_norm_d$ is the average intensity at a region defined around the depth d for the normal frame, and $Inten\_noise_d$ is the average intensity at a region defined around the depth d for the noise frame. In another embodiment, SNR at different depths are calculated with post-processed data, i.e., after log compression. In this case, the noise frame and normal frame all come out from the Rx post processing 110 and SNR can be defined as: $SNR_d = Inten.norm\ log_{d-Inten\_}noise\ log_d$, here, $Inten\_noise\ log_d$ and $Inten\_norm\ log_d$ are the average intensity in the log compressed noise and normal images correspondingly in the region defined around the depth d.

Figure 5:
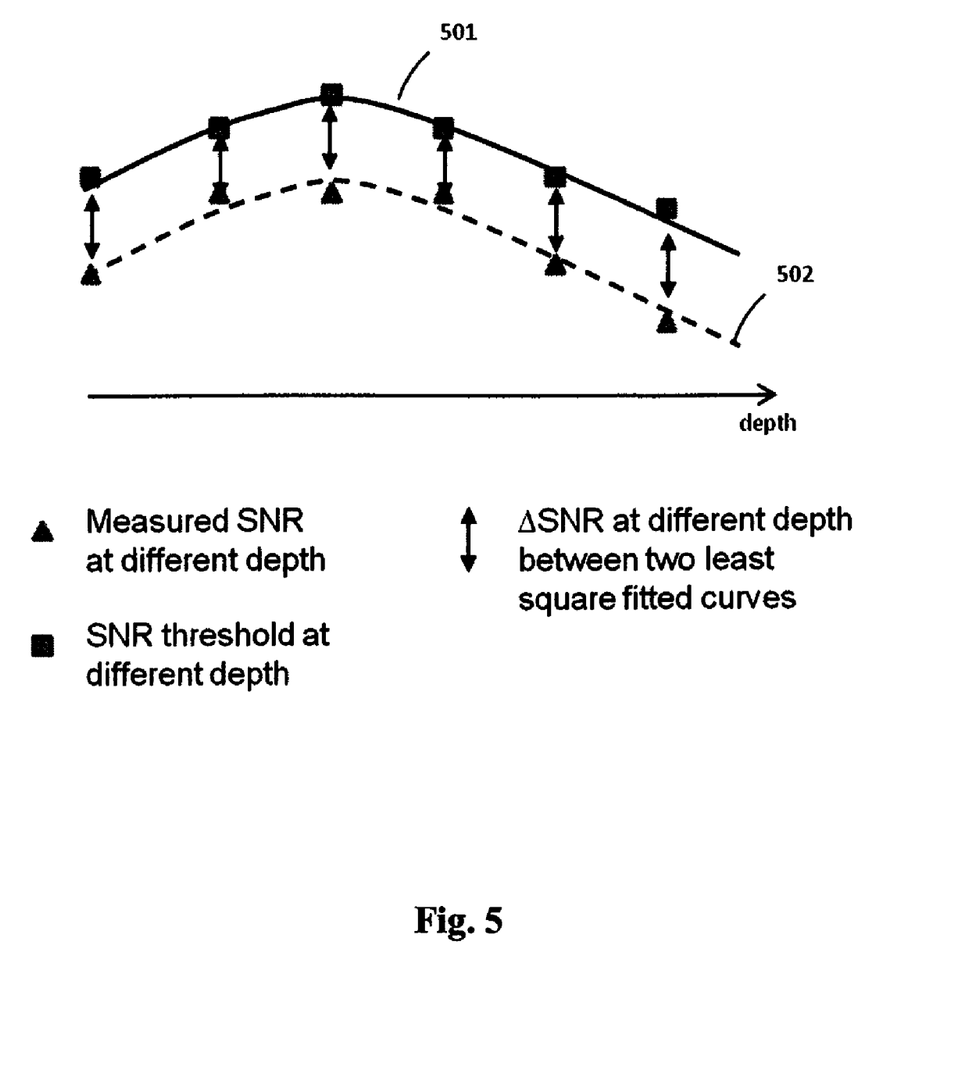
FIG. 5 is the illustration of the process to acquire ΔSNR through least square curve fitting.

The calculated SNRs at different depths (in this example, 6 different depths) are fitted with a least square curve 502 as shown in FIG. 5, then compared with a curve 501 which is a least square fit of the six pre-stored SNR thresholds. Then ΔSNR is calculated as the average difference between two fitted curves at the six depths:

$$\Delta SNR = \frac{1}{6}\sum_{1}^{6}(SNR - SNR_{threshold}).$$

A negative ΔSNR triggers the system to lower the transmit and receive center frequencies, and shrink the receive bandwidth to increase SNR in depth. The system does not randomly adjust the transmit/receive parameters toward a smaller difference with preset thresholds. Rather, the adjustment is calculated based on the value of ΔSNR, i.e., ΔSNR=−6 dB means that the signal needs to be brought up at least 6 dB to satisfy the system SNR requirement. Assume the tissue attenuation α is 0.5 dB/MHz/cm, then the system needs to reduce the transmit frequency by $$\Delta f = \frac{\Delta SNR}{2d_0 \alpha}$$

where $d_0$ is the transmit focal depth. Thus, the new frequency is $f_{new}=f_0-\Delta f$ and $f_{new}=f_{low\_limit}$ if $f_{new}$ is lower than the limit set by the transducer bandwidth. The receive center frequency is changed correspondingly. On the contrary, $\Delta SNR=6$ dB means the transmit frequency may be too low and it may result in a bad detail resolution. The system then increases the transmit/receive frequency similarly as described above to reach a new frequency $f_{new}=f_0+\Delta f$, $f_{new}=f_{up\_limit}$ if up limitation set by the transducer bandwidth has been reached.

In one embodiment of the automatic B mode imaging control process, the detail resolution at selected imaging depths including the transmit focal point is represented by the speckle size (point spread function) $PSF_d$. The speckle size is calculated using the speckle correlation method on the normal frames at the evaluation data processor 112. In multi-subtractor 114, $PSF_d$ subtracts the expected $PSF_{threshold}$ at corresponding depths for the current application. The result $\Delta PSF_d = PSF_d - PSF_{threshold}(d)$ is then sent to the feedback control 115 and the new imaging & process parameter generator 116 to adjust the imaging parameters. For example, the receive F number may be changed as:

$$F\#_{rcv}^{new}(d) = F\#_{rcv}^{old}(d) \cdot \left(1 - \frac{\Delta PSF_d}{PSF_d}\right).$$

Given the limited number of transducer elements and the element acceptance angle factor, the receive F number can only drop to a certain $_{value}min\_F\#_{rcv}^{new}$, further drop will not cause any improvement of speckle size. In this case, beyond the receive F number changes, transmit F number change may be introduced, where, at the focal depth, $$F\#_{tx}^{new} = F\#_{tx}^{old} \cdot \left(1 - \frac{\Delta PSF_{foc}}{PSF_{foc}}\right).$$

In one embodiment of this disclosed technology, the detail resolution uniformity is calculated as:

$$u = \frac{1}{M} \sum_{n=-M/2}^{M/2-1} \left(\frac{PSF_{n\Delta d}}{PSF_0}\right),$$

$M \cdot \Delta d = 1/3 \cdot d$. Here, d is the total image depth, $PSF_{n\Delta d}$ is the speckle size at depth (n$\Delta$d+focal_depth), and $PSF_0$ is the speckle size at the focal depth. A smaller u value means better uniformity, and a bigger u value means worse uniformity. In multi-subtractor 114, $\Delta u=u-u\_threshold$. $\Delta u$ is used to adjust the transmit F number, for example $F_{n+1}=(1+\sqrt{\Delta u})F_n$. Thus, when $\Delta u>0$, a bigger F number is expected so the focal region size is increased for a better uniformity.

To reach the expected performance, both detail resolution uniformity and detail resolution are used to adjust the transmit F number. As described in the above sections, since the clinical importance of detail resolution uniformity is greater than detail resolution, when the adjustments do not equal, or the adjustments may cause interference, the adjustment based on the detail resolution uniformity is selected. At step 214 in FIG. 4, the system sends any of the adjusted imaging parameters discussed above to the system control, and then goes back to step 204 and starts a new iteration. This process continues until an optimal condition is satisfied or a maximum number of iteration times is reached.

Another application example is automated Color Flow imaging. When a user turns on Color Flow (CF) imaging or moves the image region of interest (ROI) during CF imaging, the system automatically adjusts one or more CF imaging parameters to get a desired optimal performance. For this application, the system reaches the desired CF imaging performance through two feedback control processes. In the first feedback control process, the system applies the B mode type adjustments described above for basic CF image quality such as a good CF SNR, a good CF image uniformity, etc. In the second feedback control process, a good CF sensitivity is desired and the system adjusts one or more color flow processing parameters such as the pulse repetition frequency (PRF), the wall filter cutoff frequency, and the wall filters, etc., for this purpose. The CF sensitivity (CSEN) is calculated based on the ratio of the area of color region $S_{color}$ (i.e., the number of pixels that are assigned as color pixel) to the area of the overall selected ROI region $S_{ROI}$ (i.e., the total number of pixels in the ROI region) as: $CSEN=S_{color}/S_{ROI}$. Notice that CSEN is application dependent. The CSEN threshold may be defined in two ways. One way is to set it on a clinically determined value at that particular application. The other way is to set it on the on-the-fly vessel identification. In the second way, the system applies some image segmentation techniques on the currently acquired B mode image to extract the vessel from the surrounding tissue inside the ROI, then calculates the expected CSEN with the assumption that the vessel should be filled in by color flow: $CSEN_{threshold}=S_{vessel}/S_{ROI}$. Given the segmentation method credibility, a tolerance value is also set correspondingly to reflect the accuracy of the segmentation result. The second way can be used in big vessel cases where segmentation of blood vessels is easier. At multi-subtractor comparator 114, $\Delta CSEN=CSEN-CSEN_{threshold}$ is calculated. In case that $\Delta CSEN<0$, color PRF is reduced and the wall filter cutoff frequency may be shift down to improve CSEN. When $\Delta CSEN>0$, the color may be overwriting the vessel wall and the PRF is increased and the wall filter cutoff frequency may be shift up to reduce the amount of color in the ROI. Here, the amount of PRF adjustment is also based on $\Delta CSEN$.

$$PRF_{n+1} = PRF_n + \frac{\Delta CSEN}{CSEN_{threshold}} * \alpha * PRF_n.$$

Figure 6:
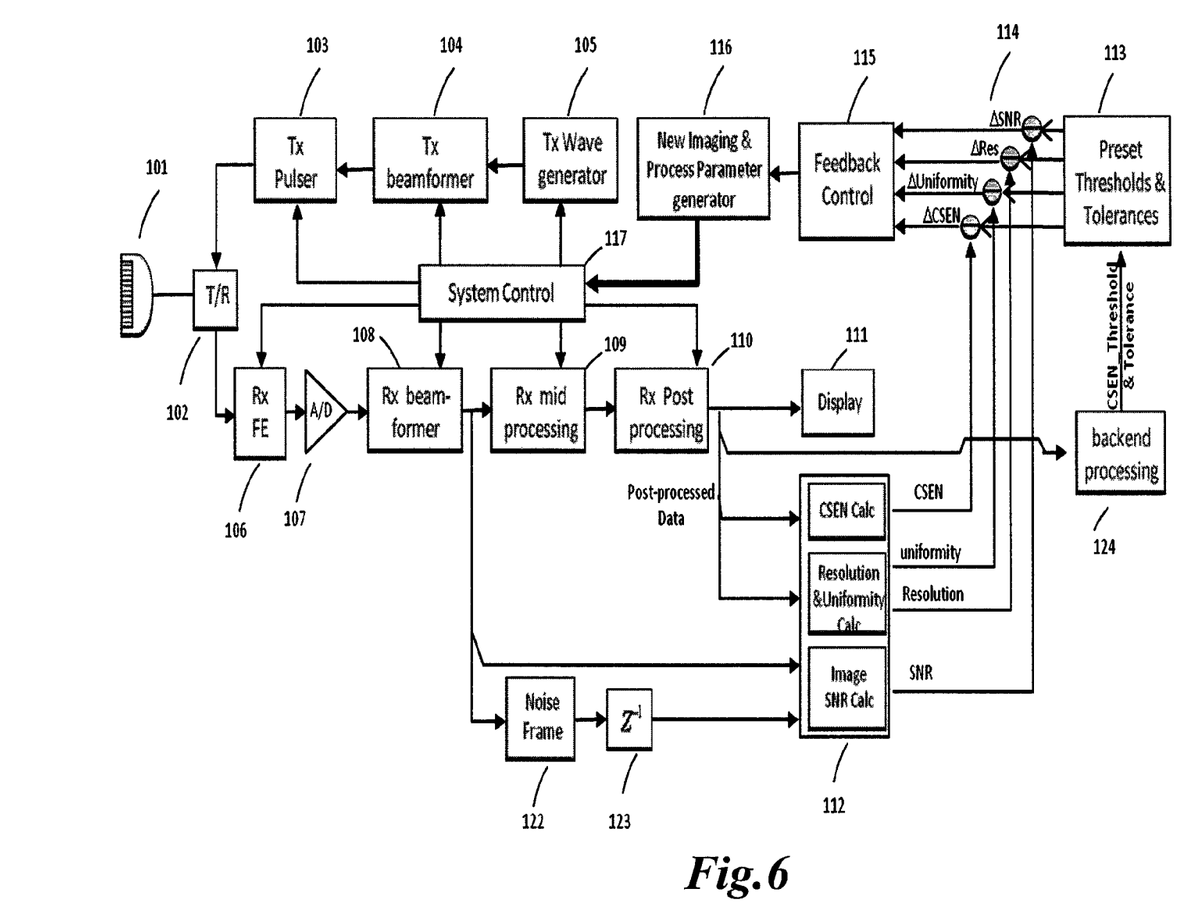
FIG. 6 is a configuration block diagram of one embodiment of a system feedback control loop for automated Color Flow imaging.

$\alpha$ is a parameter that links the $\Delta CSEN$ with PRF change and is determined empirically. FIG. 6 shows one exemplary configuration block diagram of this automated CF imaging application. An added backend processing block 124 takes in the on-the-fly B mode image and Color ROI generated in Rx post processing block 110, segments the image to extract the vessel inside ROI and calculates the CSEN threshold for comparison at multi-subtractor 114 and set the tolerance as described above for the feedback control 115 and the new imaging & process parameter generator 116. In case the segmentation does not work, a pre-stored application based CSEN threshold is used.

Figure 7:
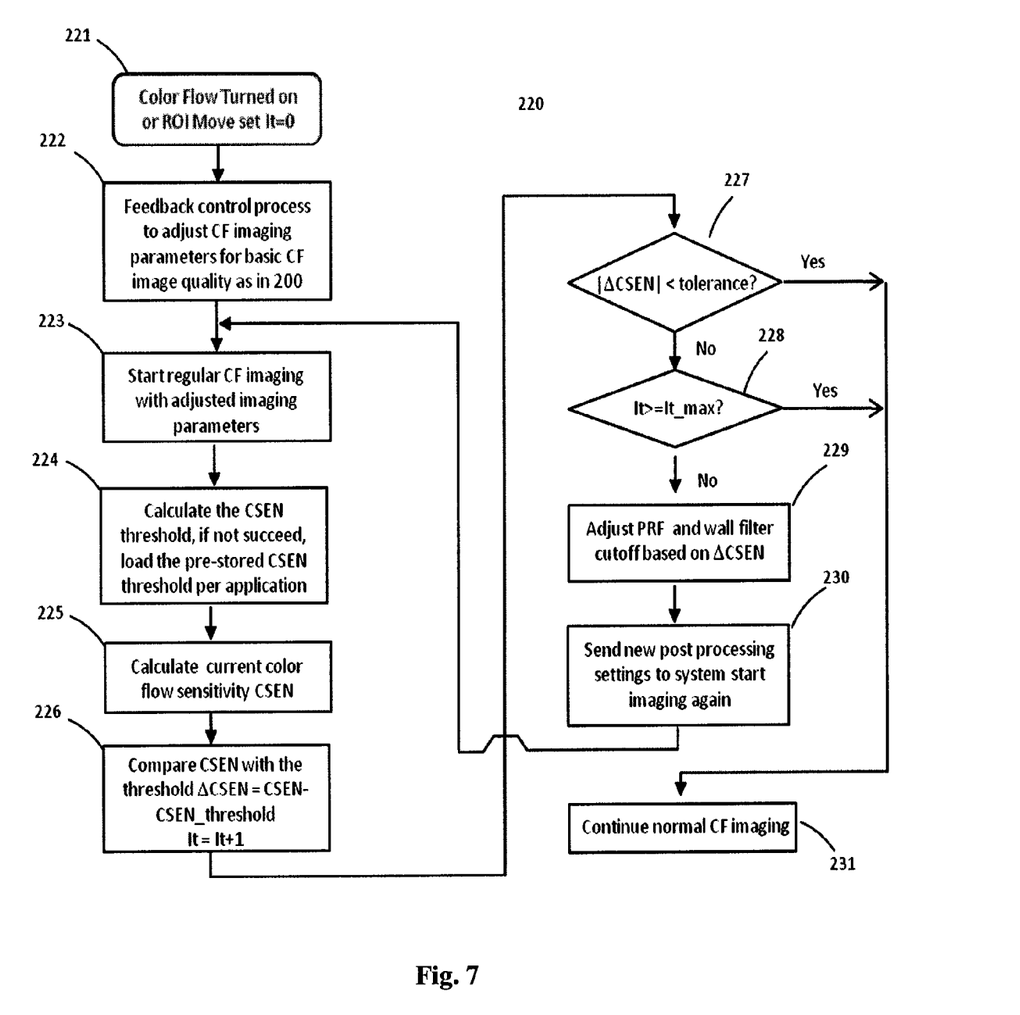
FIG. 7 is a workflow diagram of ROI change for automated Color Flow imaging in accordance with one embodiment of the present disclosed technology.

FIG. 7 shows the detail workflow 220 of one embodiment of a color flow change. It includes two feedback control processes. The general imaging parameters for Color Flow mode, such as the transmit waveforms, the receive filtering center frequency, the transmit/receive aperture controls (F numbers), etc., are adjusted first through a feedback control process in step 222 to satisfy the Color Flow general requirements on SNR, image resolution, and image uniformity. The feedback control adjustment process in step 222 follows the workflow 200 shown in FIG. 4. Color flow imaging is treated as a special B mode imaging with transmit and receive limited in the CF ROI. Different from regular Color Flow imaging, no repeat ensemble firings at one beam location are performed. Consequently, after CF mid processing, which is similar to B mode mid processing, instead of color flow post-processing to extract phase information, regular B mode post processing such as envelope detection, log compression is applied to get a B mode type image in the CF ROI for SNR in depth, resolution in depth and image uniformity calculations. In CF imaging, the expected value of pre-stored thresholds, SNR in depth, image resolution in depth, image uniformity, etc., are very different from the threshold values in B mode. For example, the CF SNR is typically set to be at least 10dB higher than the B mode SNR at the same depth, and the u_threshold is smaller in CF than in B mode resulting in a more strict uniformity requirement. After the system reaches a stable response for these general performance requirements, in step 223, regular CF imaging starts with the adjusted imaging parameters. This is the start of a new feedback control process for which the CSEN performance is the target. In step 224, using the B mode data and Color ROI, the current expected CSEN threshold is calculated. If this does not succeed, the pre-stored application based CSEN threshold is loaded instead. At step 225, the current CF CSEN is calculated using the Color Flow data, and compared with the CSEN threshold to get ΔCSEN in 226. In steps 227 and 228, ΔCSEN and the number of iteration times are checked to decide if current Color Flow setting is good enough or if a maximum number of iteration times has been reached. If not, the system adjusts the color PRF and the wall filter cutoff frequency in step 229 and applies these newly adjusted parameters for Color Flow post processing in step 230. The system then goes back to step 223 to start this feedback control loop again until the CF imaging sensitivity performance reaches the requirement or the maximum number of iteration times is reached, then the system goes to step 231 for regular CF imaging.

In most applications of this closed-loop feedback control imaging system, such as B mode, CF mode, and Pulse Doppler mode imaging, given the values of Δparameters, the system is able to adjust imaging parameters with a predefined quantitative or qualitative scheme to drive Δparameters toward zero. In certain applications, given the values of the Δparameters, there is no predefined quantitative or qualitative scheme that can for sure drive the Δparameters toward zero. In this case, the system adjusts the imaging parameters based on the comparison between two consequent sets of Δparameters: Δparameters($I_T$) and Δparameters($I_{T-1}$) to reach a stable response, thus, to meet an expected performance. Δparameters($I_T$) is the Δparameters at iteration time $I_T$. Δparameters ($I_{T-1}$) is the Δparameters at previous iteration time $I_{T-1}$.

One example illustrating one use of the above disclosed ultrasound system is to adjust the sound speed in breast imaging. Breast tissue is quite different from other tissue in human body due to its highly heterogeneous characteristics. It has been found that the speed of sound in breast tissue varies a lot for different breasts. The sound speed variation severely affects the beamforming quality, since both transmit and receive beamforming are based on a predetermined sound speed, typically, 1540 m/sec. The automatic imaging system described herein solves this issue easily, even though the correct speed of sound for each breast is unknown in the beginning of the scan.

Figure 8:
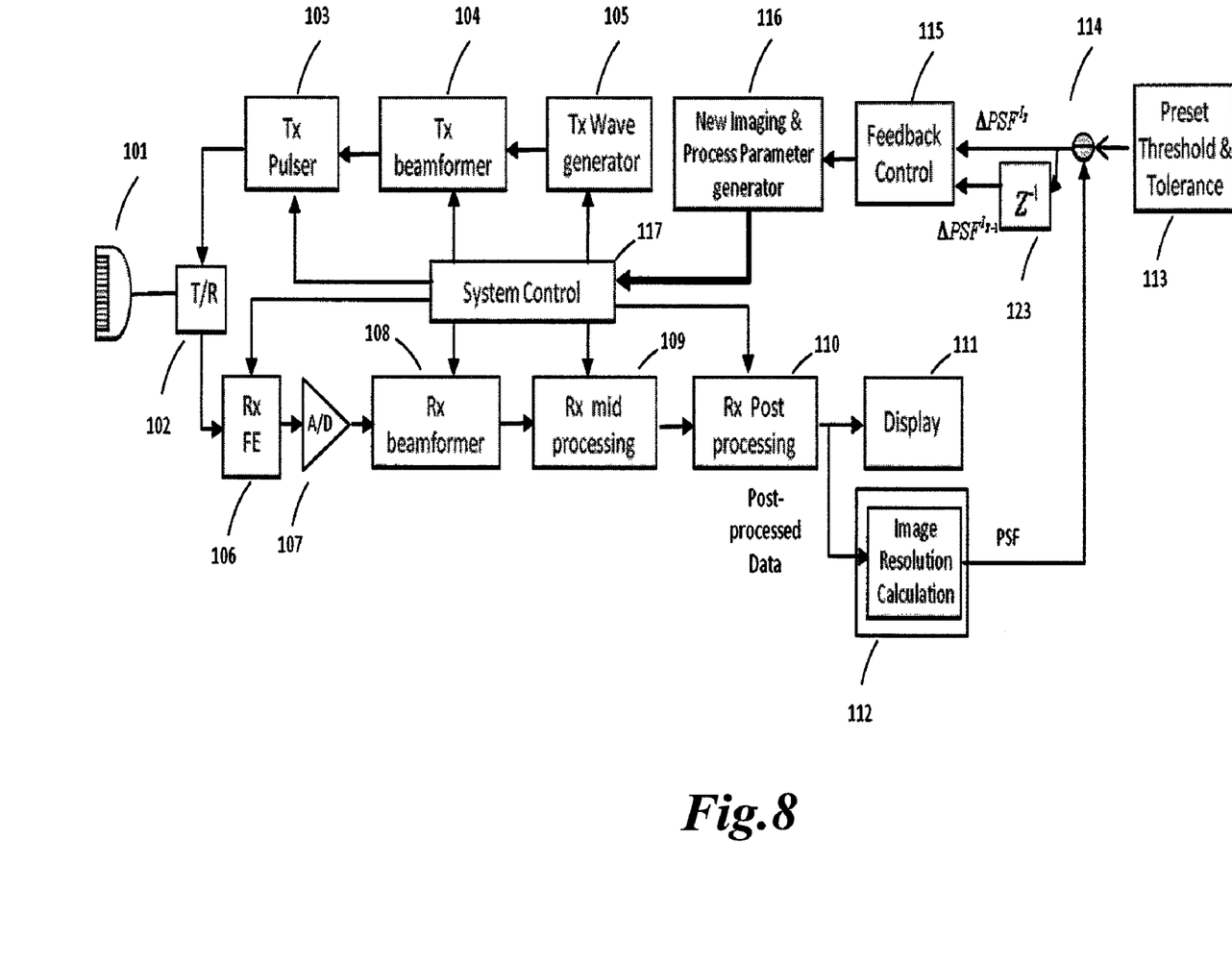
FIG. 8 is a configuration block diagram of a system feedback control loop for sound speed adjustment.

FIG. 8 shows the block diagram of the feedback control system configuration for the sound speed adjustment. In this application, the image detail resolution in a depth d, as defined by $PSF_d$, is used to adjust the speed of sound. The performance evaluator 112 uses a post-processed image to calculate $PSF_d$. In FIG. 8, a one step delay block 123, $Z^{-1}$ is added after multi-subtractor 114. It delays the $\Delta PSF_d$ for one iteration step, so $\Delta PSF_d^{I_T}$ and $\Delta PSF_d^{I_{T-1}}$ are sent to the feedback control block 115 together to determine the adjustment amount and the direction. Here, $I_T$ is the iteration index.

Figure 9:
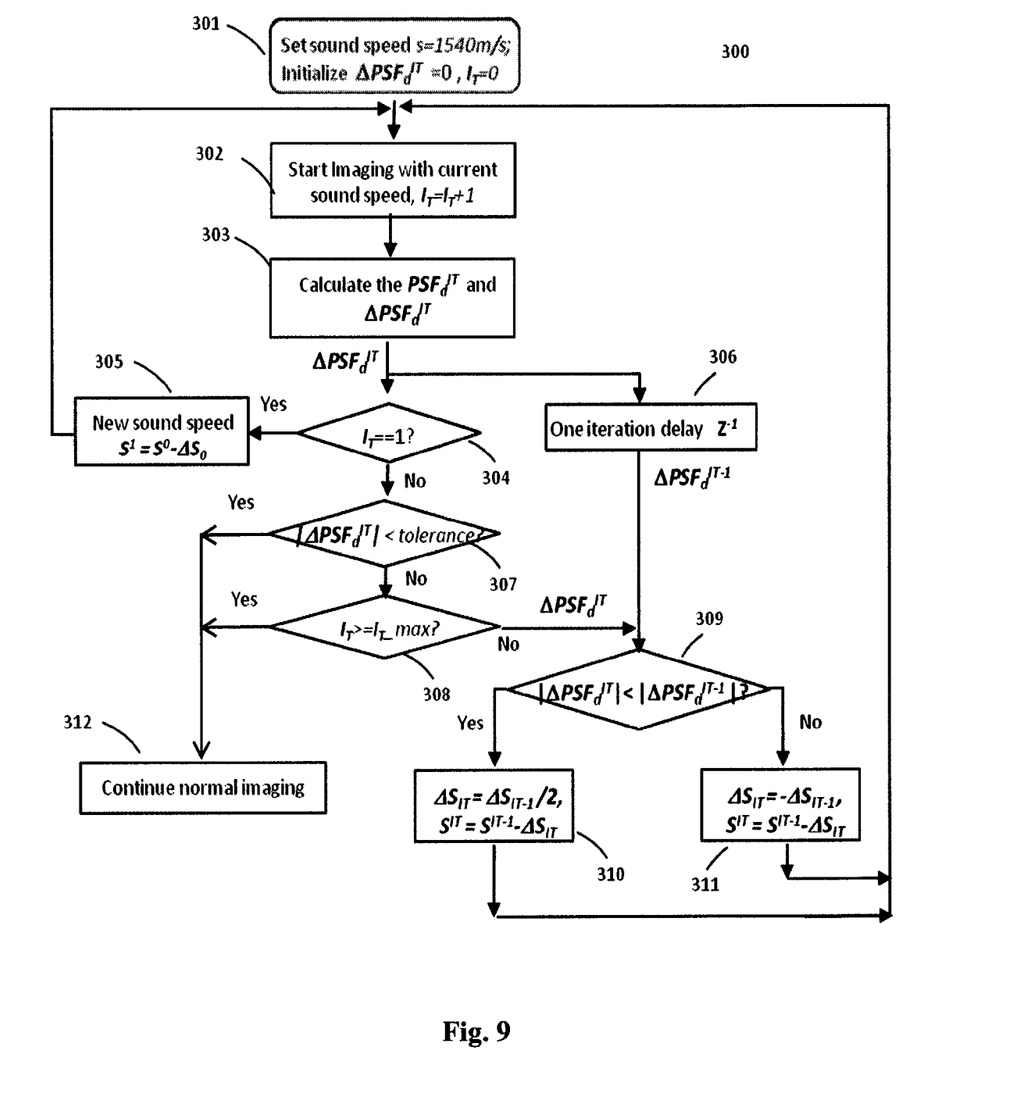
FIG. 9 is the detail work flow of the sound speed adjustment in accordance with an embodiment of this disclosed technology.

FIG. 9 gives the detail work flow 300 of one embodiment of the speed sound adjustment. In step 301, the system sets a predefined sound speed, e.g., 1540 m/sec, initializes $\Delta PSF_d^0$ with 0, and sets iteration index $I_T$=0. In step 302, the system starts imaging for a breast scan and increases the index of $I_T$ as $I_T$=$I_T$+1. In step 303, the resulting normal B mode image is sent to the performance evaluator 112 to calculate the image detail resolution $PSF_d^{I_T}$. Then $\Delta PSF_d^{I_T}$=$PSF_d^{I_T}$−$PSF_{threshold}$ (d) is calculated in multi-subtractor 114 with $PSF_{threshold}$ as the expected detail resolution defined empirically. In step 304, the system checks if it is the first time iteration ($I_T$=1). If yes, in step 305, the system decreases the speed of sound in a predefined amount $\Delta S_0$, S'=S−$\Delta S_0$, then goes back to step 302 to start a new iteration. If it is not the first time iteration ($I_T$≠1), the system checks if $|\Delta PSF_d^{I_T}|$<Tolerance and if the maximum number of iteration times is reached (It>=It_max) in steps 307 and 308. If either condition is satisfied, the system goes out of the feedback iteration loop and goes directly to step 312 for normal imaging with current sound speed. If neither condition is satisfied, in step 309, the system compares $\Delta PSF_d^{I_T}$ and $\Delta PSF_d^{I_{T-1}}$ which is acquired in step 303 and delayed by one iteration in step 306. Together with step 310 and step 311, the system fulfills a logic as described below:

If $|\Delta PSF_d^{I_T}|$<$|\Delta PSF_d^{I_{T-1}}|$, then $\Delta S_{I_T}$=$\Delta S_{I_{T-1}}$/2, $S^I_{I_T}$−$\Delta S_{I_T}$.
If $|\Delta PSF_d^{I_T}|$>$|\Delta PSF_d^{I}_{T-1}|$, then $\Delta S_{I_T}$=−$\Delta S_{I_{T-1}}$, $S^{I_T}$=$S^{I_{T-1}}$−$\Delta S_{I_T}$.

Then the new sound speed $S^{I_T}$=$S^{I_{T-1}}$−$\Delta S_{I_T}$ is set and the system goes back to step 302 with this new sound speed to start a new feedback control iteration. This feedback iteration continues until absolute value of $\Delta PSF_d$ is smaller than the predefined tolerance or the maximum number of iteration times is reached.

In conclusion, this negative feedback control architecture and process can be applied to almost all other ultrasound imaging modes, such as Pulse Wave Doppler imaging, Continuous Wave Doppler imaging, M mode imaging, Elastography imaging, 4D imaging, etc. Further, beside the imaging parameters mentioned above, many other imaging parameters can be used. For example, the system power may be adjusted to keep a low level ultrasound power output while maintaining a big enough SNR for imaging. In case of advanced imaging such as steered spatial compounding, the steering angles of different image components may be adjusted automatically based on the grating lobe level and the speckle reduction effect. As mentioned in the above sections, the system can always reconfigure the feedback control loop architecture to fit different applications automatically and allow a smooth transition between the configurations. For example, when a user starts with B mode imaging, the system loads the configuration for automated B mode imaging described above into the feedback control loop and makes adjustments to reach an optimal B mode image quality for the target. If, after a while, the user turns on CF imaging, the system then reconfigures the feedback control architecture for automated CF imaging as described above and tries to reach an optimal CF imaging performance for the target. All these configurations are pre-stored in the feedback architecture configuration & control 150.

Although the presented embodiment of the ultrasound imaging system has been disclosed, it will be appreciated that changes could be made without departing from the scope of the invention. For example, although the performance evaluator 112, the multi-subtractor 114, the feedback control 115, the new imaging & process parameter generator 116, and the feedback architecture configuration & control 150 are shown as separate components, it will be appreciated that part or whole of the functions performed by these components may be performed by a general or special purpose microprocessor in accordance with a sequence of programmed instructions stored in a computer-readable storage medium.

The invention claimed is:

1. An ultrasound imaging system, comprising:
   a transmitter configured to deliver one or more ultrasound pulses to a patient;
   a receiver configured to receive and process one or more ultrasound echoes from the patient;
   a systems control that is configured to cause the transmitter to deliver the one or more ultrasound pulses to the patient and the receiver to receive and process the one or more ultrasound echoes from the patient according to one or more imaging parameters;
   an imaging performance evaluator that is configured to determine a plurality of performance evaluation parameters from the one or more ultrasound echoes;
   a negative feedback controller that is configured to:
      receive the plurality of performance evaluation parameters;
      determine quantitative differences between the plurality of performance evaluation parameters and corresponding performance evaluation parameter thresholds, wherein the corresponding performance evaluation parameter thresholds represent a desired imaging performance; and
      modify one or more of the imaging parameters according to one or more mathematical functions of the determined quantitative differences to cause one or more performance evaluation parameters determined from subsequent echoes to approach the corresponding performance evaluation parameter thresholds, wherein a predetermined importance value is associated with each of the performance evaluation parameters, and wherein the one or more imaging parameters are modified also in accordance with the importance values of the performance evaluation parameters;
   a memory unit that is configured to store the performance evaluation parameter thresholds; and
   a feedback architecture configuration & control unit that is programmed to implement different imaging performance evaluators and to reconfigure the negative feedback controller for different imaging applications, wherein the different imaging applications include one or more of different imaging modes, imaging different patient types, and imaging different parts of a human body.

2. The ultrasound imaging system of claim 1, wherein the performance evaluation parameter thresholds include tolerance ranges, and wherein the negative feedback controller is configured to modify one or more of the imaging parameters as one or more mathematical functions of the determined quantitative differences until the differences between the one or more performance evaluation parameters and the corresponding performance evaluation parameter thresholds are within the tolerance ranges.

3. The ultrasound imaging system of claim 2, wherein the tolerance ranges correlate to the importance values of the corresponding performance evaluation parameters in an inversely proportional way, and wherein the one or more imaging parameters are modified in accordance with the tolerance ranges of the corresponding performance evaluation parameter thresholds.

4. The ultrasound imaging system of claim 2, wherein more than one of the performance evaluation parameters require modification of the same imaging parameter, wherein the negative feedback controller is configured to select a modification for the imaging parameter, and wherein the selected modification is associated with the performance evaluation parameter having the least tolerance range among all performance evaluation parameters that require modifications to the same imaging parameter.

5. The ultrasound imaging system of claim 2, wherein the tolerance ranges are predetermined, defined at a customer site, or dynamically calculated with current received echoes.

6. The ultrasound imaging system of claim 1, wherein the negative feedback controller is configured to modify one or more of the imaging parameters until the differences between the one or more performance evaluation parameters and the corresponding performance evaluation parameter thresholds are within tolerance ranges or the one or more imaging parameters have been modified a predetermined number of times.

7. The ultrasound imaging system of claim 1, wherein the feedback architecture configuration & control unit stores a plurality of different configurations where each configuration defines a set of performance evaluation parameters and corresponding evaluation processes for the imaging performance evaluator, control logic for the negative feedback controller, and a plurality of performance evaluation parameter thresholds with corresponding tolerance ranges,
   wherein the control logic includes a decision scheme that determines if a desired performance requirement has been reached and, in case of multiple desired performance requirements, a decision scheme that evaluates the importance values of the performance evaluation parameters and determines an order of priority for selecting and modifying the one or more imaging parameters to satisfy the multiple desired performance requirements, and
   wherein the control logic further includes mathematical equations among which at least some are functions of the determined quantitative differences.

8. The ultrasound imaging system in claim 1, wherein the feedback architecture configuration & control unit configures the negative feedback controller to periodically adjust one or more of the imaging parameters to maintain a desired imaging performance.

9. The ultrasound imaging system of claim 1, wherein the performance evaluation parameters include one or more of: image signal to noise ratio (SNR), image detail resolution, image contrast resolution, image contrast resolution uniformity, image detail resolution uniformity, color flow sensitivity, Pulse Wave Doppler sensitivity, Continuous Wave Doppler sensitivity, system gain uniformity, imaging frame rate, or micro-bubble sensitivity.

10. The ultrasound imaging system of claim 1, wherein the importance values are represented by priority numbers.

11. The ultrasound imaging system of claim 10, wherein more than one of the performance evaluation parameters require modification of the same imaging parameter, wherein the negative feedback controller is configured to select a modification for the imaging parameter, and wherein the selected modification is associated with the performance evaluation parameter having the highest priority number among all performance evaluation parameters that require modifications to the same imaging parameter.

12. The ultrasound imaging system of claim 1, wherein the performance evaluation parameters are separated into multiple sets that are independent of each other, and the negative feedback controller is configured to modify the one or more imaging parameters belonging to each set separately or in an order of priority such that the performance evaluation parameters approach a desired imaging performance for each set separately.

13. The ultrasound imaging system of claim 1, wherein the performance evaluation parameters are separated into multiple sets that are dependent on each other, and wherein the negative feedback controller is configured to modify the one or more imaging parameters for each set, in which the sets are processed in an order of priority based on the set dependence, such that the performance evaluation parameters approach a desired imaging performance.

14. The ultrasound imaging system of claim 1, wherein the memory unit is further configured to store a tolerance value for each performance evaluation parameter threshold.

15. The ultrasound imaging system of claim 1, wherein the performance evaluation parameter thresholds are predetermined, defined at a customer site, or dynamically calculated with current received echoes.

16. The ultrasound imaging system in claim 1, wherein the negative feedback controller is configured to utilize two sequential differences between the performance evaluation parameters and the corresponding thresholds to determine a direction and amount for the modification of the one or more imaging parameters, wherein one of the two sequential differences is calculated based on current received echoes and the other of the two sequential differences is calculated based on previous received echoes.

17. The ultrasound imaging system of claim 1, wherein the one or more received echoes include one or more of a pre-beamsummed per channel radio frequency data, a beamsummed radio frequency data, a demodulated in-phase and quadrature data, and a post-processed image.

18. The ultrasound imaging system of claim 1, wherein the negative feedback controller further includes:
a multi-subtractor configured to quantitatively compare the plurality of performance evaluation parameters with the performance evaluation parameter thresholds through a subtraction operation and outputs the determined quantitative differences;
a feedback control unit configured to determine if a desired imaging performance is reached or if further modification of one or more imaging parameters is necessary based on the determined quantitative differences; and
a new imaging & process parameter generator configured to modify one or more of the imaging parameters as one or more mathematical functions of the determined quantitative differences to cause one or more performance evaluation parameters determined from subsequent echoes to approach the corresponding performance evaluation parameter thresholds,
wherein the feedback control unit is further configured to determine an order of priority for selecting and applying modifications to the one or more imaging parameters based on the importance values and/or dependencies of the performance evaluation parameters when more than one performance evaluation parameters are employed.

19. The ultrasound imaging system of claim 1, wherein a predetermined dependence characteristic is further associated with each of the one or more performance evaluation parameters, and wherein the one or more imaging parameters are modified in accordance with both the importance values and the dependence characteristics of the performance evaluation parameters.

20. The ultrasound imaging system of claim 19, wherein the predetermined importance values and dependence characteristics of the performance evaluation parameters reflect a relative importance and interdependence of the performance evaluation parameters and the imaging performance aspects they represent for achieving a desired imaging performance.

21. The ultrasound imaging system of claim 1, wherein the negative feedback controller is configured to determine which of the one or more imaging parameters to modify based on the importance values of the performance evaluation parameters.

22. The ultrasound imaging system of claim 1, wherein at least one of the imaging parameters is subject to multiple modifications required from multiple performance evaluation parameters, and wherein the negative feedback controller is configured to determine which modification to apply to the at least one imaging parameter based on the importance values of the multiple performance evaluation parameters.

23. An ultrasound imaging system, comprising:
a transmitter configured to deliver one or more ultrasound pulses to a patient;
a receiver configured to receive and process one or more ultrasound echoes from the patient;
a systems control configured to cause the transmitter to deliver the one or more ultrasound pulses to the patient and the receiver to receive and process the one or more ultrasound echoes from the patient according to one or more imaging parameters;
an imaging performance evaluator configured to determine a plurality of performance evaluation parameters from the one or more ultrasound echoes;
a negative feedback controller comprising:
a negative feedback control unit, wherein the negative feedback control unit is configured to:
separate the plurality of performance evaluation parameters into two or more groups;
for each group, quantitatively compare the performance evaluation parameters with corresponding performance evaluation parameter thresholds, wherein the corresponding performance evaluation parameter thresholds represent a desired imaging performance; and
determine a priority order for selecting and modifying the one or more imaging parameters in each group and among the groups in accordance with predetermined importance values and dependence characteristics corresponding to the one or more performance evaluation parameters,
wherein the predetermined importance values and dependence characteristics represent a relative importance and interdependence of the performance evaluation parameters and the imaging performance aspects they represent for achieving the desired imaging performance; and
a new imaging & process parameter generator configured to modify the one or more imaging parameters as one or more mathematical functions of the quantitative comparisons according to the selection and priority order determined by the negative feedback control unit to cause one or more performance evaluation parameters determined from subsequent echoes to iteratively approach the corresponding performance evaluation parameter thresholds;

a memory unit configured to store the performance evaluation parameter thresholds; and a feedback architecture configuration & control unit programmed to implement different imaging performance evaluators, and to reconfigure the negative feedback control unit and the new imaging & process parameter generator for different imaging applications, wherein the different imaging applications include one or more of different imaging modes, imaging different patient types, and imaging different parts of a human body.

24. The ultrasound imaging system of claim 23, wherein the new imaging & process parameter generator is configured to modify the one or more imaging parameters as one or more mathematical functions of differences between quantitative comparisons from current received echoes and quantitative comparisons from previous received echoes.

* * * * *